US010071122B2

(12) United States Patent
Greene et al.

(10) Patent No.: US 10,071,122 B2
(45) Date of Patent: Sep. 11, 2018

(54) HEAT-EXTRACTED OMENTUM EXTRACTS, COMPOSITIONS, METHODS OF PREPARING AND USES THEREOF

(75) Inventors: James A. Greene, Sunnyvale, CA (US); Jerad Busch, Murphysboro, IL (US); George Wrape, Jr., Cape Girardeau, MO (US); Jonathan D. Klein, Commack, NY (US)

(73) Assignee: COOPERLABS LIMITED, Ventura, CA (US)

( * ) Notice: Subject to any disclaimer, the term of this patent is extended or adjusted under 35 U.S.C. 154(b) by 133 days.

(21) Appl. No.: 14/007,303

(22) PCT Filed: Mar. 25, 2011

(86) PCT No.: PCT/US2011/030059
§ 371 (c)(1),
(2), (4) Date: Sep. 24, 2013

(87) PCT Pub. No.: WO2012/134433
PCT Pub. Date: Oct. 4, 2012

(65) Prior Publication Data
US 2014/0017334 A1    Jan. 16, 2014

(51) Int. Cl.
| | |
|---|---|
| *A61K 35/38* | (2015.01) |
| *A61K 35/12* | (2015.01) |
| *A61K 35/37* | (2015.01) |
| *A61Q 7/00* | (2006.01) |
| *A61Q 19/00* | (2006.01) |
| *A61K 8/98* | (2006.01) |
| *A61K 38/18* | (2006.01) |
| *A61K 35/35* | (2015.01) |

(52) U.S. Cl.
CPC .............. *A61K 35/37* (2013.01); *A61K 8/981* (2013.01); *A61K 35/35* (2013.01); *A61K 38/1866* (2013.01); *A61Q 7/00* (2013.01); *A61Q 19/00* (2013.01); *A61K 2800/91* (2013.01)

(58) Field of Classification Search
None
See application file for complete search history.

(56) References Cited

U.S. PATENT DOCUMENTS

| | | | |
|---|---|---|---|
| 4,776,173 A | 10/1988 | Kamarei et al. | |
| 2004/0166170 A1* | 8/2004 | Hunter | A61K 8/981 424/582 |
| 2009/0163990 A1* | 6/2009 | Yang | A61L 27/22 623/1.15 |
| 2009/0191127 A1 | 7/2009 | Saini | |

FOREIGN PATENT DOCUMENTS

| | | |
|---|---|---|
| EP | 2688576 | 12/2014 |
| JP | 63-502345 | 9/1988 |
| JP | 1-502591 | 9/1989 |
| WO | WO 89-10114 | 11/1989 |
| WO | WO2012134433 | 10/2012 |

OTHER PUBLICATIONS

Vernik et al., "Omentum: Power to Heal and Regenerate," Int'l J. of Artificial Organs, vol. 30, No. 2, pp. 95-99 (2007).
Supplementary European Search Report, EP Application No. 11862828. 8, 7pp. (dated Oct. 30, 2014).
Japanese Office action for Japanese Patent Application No. 2014-501052 (and its English translation), 10 pp. (dated Nov. 14, 2014).
Office Action for Canadian Patent Application No. 2,830,877, dated Oct. 31, 2017 (4 pages).
International Search Report and Written Opinion, dated Dec. 22, 2011, by the Korean Intellectual Property Office for corresponding PCT Patent Application No. PCT/US2011/030059, 13 pages.

\* cited by examiner

*Primary Examiner* — Christopher R Tate
*Assistant Examiner* — Randall Winston
(74) *Attorney, Agent, or Firm* — Klarquist Sparkman LLP

(57) ABSTRACT

Disclosed herein are compositions including an extract of mammalian omentum wherein the extract is a liquid portion of the mammalian omentum, such as an oil, extracted when the omentum is heated to a temperature of between 210 and 240 degrees Fahrenheit. Also disclosed are methods of making a composition including an extract of mammalian omentum wherein the method includes heating mammalian omentum to a temperature of between 212 degrees Fahrenheit and 225 degrees Fahrenheit, such as 215 degrees Fahrenheit and 220 degrees Fahrenheit. Methods of use of the disclosed extracts and compositions are provided including methods of inducing or enhancing angiogenesis, methods of improving skin quality and methods of promoting hair growth and/or inhibiting hair loss.

8 Claims, 7 Drawing Sheets

HEAT-EXTRACTED OMENTUM EXTRACTS, COMPOSITIONS, METHODS OF PREPARING AND USES THEREOF

CROSS REFERENCE TO RELATED APPLICATIONS

This is the U.S. National Stage of International Application No. PCT/US2011/030059, filed Mar. 25, 2011.

FIELD OF THE DISCLOSURE

Disclosed herein are methods of extracting omental lipids and therapeutic and cosmetic uses comprising the extracted omental lipids along with compositions comprising the same.

BACKGROUND

Omentum is a nutrient-rich sheet of fat that is attached to the stomach and transverse colon area of most if not all mammals (this includes feline, bovine, ovine and porcine omentum). In general, the greater omentum hangs down over the intestines in the abdominal cavity while the lesser omentum is attached to the top edge of the stomach and stretches to the underside of the liver.

Omental lipid material is known to possess angiogenic factors that stimulate tissue vascularization, as disclosed in e.g., U.S. Pat. No. 5,798,386, to Nudelman, and U.S. Pat. No. 5,710,175 to Nudelman, which aids growth and healing. Thus, omental lipid extracts conventionally extracted using organic solvents have been disclosed as beneficial to treat a number of conditions such as epithelial wound healing in U.S. Pat. No. 4,767,746 to Catsimpoolas (also see, for additional angiogenic effects, Cartier et al., *J. Thorac. Cardiovasc. Surg.* 99:264-268, 1990; Goldsmith et al., *J. Amer. Med. Ass'n.* 252: 2034-2036, 1984; Levy et al., *Eur. Surg. Res.*, 30: 138-143, 1998; U.S. Pat. Nos. 4,699,788, 4,710, 490, 4,778,787, and 4,888,324 to Catsimpoolas; U.S. Pat. No. 4,990,333 to Lane; International Publication Nos. WO 87/01939, WO 87/03811, and WO 87/06136 to Catsimpoolas); and for a number of uses such as in softening, moisturizing and smoothing of skin and reduction of calluses and white spots thereon as stated by U.S. Pat. No. 4,879,114 to Catsimpoolas.

As noted, the conventional method of extracting beneficial lipid factors from omental material is through the use of organic solvents, primarily hexane, at temperatures well below 100 degrees Celsius. This method was disclosed in "Lipid Angiogenesis Factor From Omentum" by Harry S. Goldsmith et al. (1984) *J. Amer. Med. Ass'n.* 252: 2034, which nearly all other disclosures of omental extraction follow, as can be seen for example in U.S. Pat. No. 4,778,787 to Catsimpoolas and U.S. Pat. No. 4,776,173 to Kamarei. The use of organic solvents in an extraction process can pose risks in the extraction process and also may not be palatable to consumers having concerns regarding the chemicals to which they expose their bodies.

Hunter discloses a method of processing omental material without disclosing the use of an organic solvent in US 2004/0166170 A1. However, Hunter does not enable or fully describe any process for obtaining a particular end product. In the Hunter application, Hunter discloses a method of processing raw omental material at a wide temperature range of between 100 degrees Fahrenheit (referenced herein in some cases as "F") and 300 degrees Fahrenheit and a preferred embodiment in which omental material should first be heated at a starting temperature of 160 degrees Fahrenheit and the temperature should be raised by 20 degrees Fahrenheit every 2 hours for between 7 and 8 hours (which would result in an unknown end temperature since Hunter discloses to heat at a temperature and it is unclear what temperature is actually reached by the omental material in Hunter). Then the material is filtered by undisclosed means. It is unclear whether the filtrate or the retentate is kept. However, whatever is kept is disclosed to then be tempered at a temperature of 58 degrees Fahrenheit. Thus, Hunter at best describes heating pieces of omental material, filtering the substance, and then cooling whatever substance is kept to 58 degrees Fahrenheit. Hunter fails to enable any method or composition.

Given the above, a need exists for a method of extracting therapeutic fractions from omental materials without the use of organic solvents and for compositions comprising such components.

SUMMARY

Disclosed herein are compositions including an extract of mammalian omentum wherein the extract is a liquid portion of the mammalian omentum extracted when the omentum is heated to a temperature of between 210 and 240 degrees Fahrenheit, such as between 212 degrees Fahrenheit and 225 degrees Fahrenheit or 215 degrees Fahrenheit and 220 degrees Fahrenheit. Also disclosed are methods of making compositions comprising an extract of mammalian omentum. Methods of use of the disclosed extracts and compositions are provided including methods of inducing or enhancing angiogenesis, methods of improving skin quality and methods of promoting hair growth and/or inhibiting hair loss.

In some embodiments, a composition includes an extract of mammalian omentum wherein the extract is a liquid portion of the mammalian omentum extracted when the omentum is heated to a temperature of between 210 degrees Fahrenheit and 240 degrees Fahrenheit. In some embodiments, a composition includes an extract of mammalian omentum wherein the extract is a liquid portion of the mammalian omentum extracted when the omentum is heated to a temperature of between 212 degrees Fahrenheit and 225 degrees Fahrenheit. In some embodiments, a composition includes an extract of mammalian omentum wherein the extract is a liquid portion of the mammalian omentum extracted when the omentum is heated to a temperature of between 215 degrees Fahrenheit and 220 degrees Fahrenheit.

In some embodiments, a composition includes an extract of mammalian omentum wherein the extract is a liquid portion of the mammalian omentum extracted when the omentum is heated to a temperature of between 210 degrees Fahrenheit and 240 degrees Fahrenheit, such as any of the ranges disclosed in the prior paragraph, wherein an organic solvent is not used to extract the extract.

In some embodiments, a method of making a composition comprises heating the mammalian omentum to a temperature of between 210 degrees Fahrenheit and 240 degrees Fahrenheit and extracting the liquid portion of the heated mammalian omentum. In some embodiments of this method, heating the mammalian omentum comprises heating the mammalian omentum to a temperature of between 212 degrees Fahrenheit and 225 degrees Fahrenheit. In some embodiments, heating the mammalian omentum comprises heating the mammalian omentum to a temperature of between 215 degrees Fahrenheit and 220 degrees Fahrenheit. In some embodiments, heating the mammalian omentum comprises heating the mammalian omentum in the absence of an organic solvent.

In some embodiments, a disclosed method of making a composition further comprises preparing omentum for lipid extraction prior to heating the mammalian omentum. In some embodiments, methods of preparing omentum for lipid extraction comprise isolating omentum from a subject. In some embodiments, preparing omentum for lipid extraction comprises freezing the isolated omentum. In some embodiments, preparing omentum comprises soaking omentum in a cleaning solution. In some embodiments, preparing omentum comprises soaking omentum in a cleaning solution that is about a 2.5% saline solution. In some embodiments, preparing omentum comprises soaking omentum in a 2.5% saline solution for about 36 hours. In some embodiments, preparing omentum for lipid extraction comprises isolating omentum for a subject, freezing the isolated omentum and soaking omentum in a cleaning solution.

In some embodiments, the method of making a composition further includes purifying the liquid extracted from the omental material. For example, purifying the extracted liquid comprises filtering the extracted liquid through a filter press comprising a series of two or more 13⅝ inches diameter, 22 micron pore size filters to remove solid omentum material.

In some embodiments, the omentum is porcine omentum, but the omentum of any mammal could be used.

In some embodiments, methods of inducing or enhancing angiogenesis in a subject's tissue include administering to a subject an effective amount of any of the disclosed compositions, such as compositions made by the methods disclosed herein (such as, but not limited to those described in Examples 1-3 and/or 5), thereby inducing or enhancing angiogenesis in the subject's tissue.

In some embodiments, a method of promoting hair growth and/or inhibiting hair loss in a subject comprises administering to a subject an effective amount of the composition of any of the disclosed compositions, such as any of the disclosed compositions made by the disclosed methods (such as, but not limited to those described in Examples 1-3 and/or 5), thereby promoting hair growth and/or inhibiting hair loss in the subject.

In some examples, administering the disclosed compositions comprises topical administration, intraperitoneal injection, intravenous injection, subcutaneous injection, transdermal injection, or intramuscular injection. In some examples, the composition is administered to an area of alopecia-affected skin. In some examples, the composition is administered to the scalp of the human. In some examples, the hair loss in the subject results from a health disorder or a therapeutic treatment. Exemplary health disorders can include alopecia areata, traction alopecia, folliculitis alopecia, telogen effluvium, loose-anagen syndrome, toxic alopecia, acquired immune deficiency syndrome (AIDS), hypothroidism, hyperthyroidism, lupus erythematosus, diabetes, iron deficiency, syphilis, zinc deficiency, trichotillomania, or Cushing syndrome. In some examples, the therapeutic treatment is chemotherapy or radiation therapy.

In some embodiments, administering to a subject an effective amount of any of the disclosed compositions, such as any of the disclosed compositions made by the disclosed methods (such as, but not limited to those described in Examples 1-3 and/or 5), improves the skin quality in the subject.

The foregoing and other features of the disclosure will become more apparent from the following detailed description of a several embodiments which proceeds with reference to the accompanying figures.

DETAILED DESCRIPTION

I. Introduction

Figure 1:
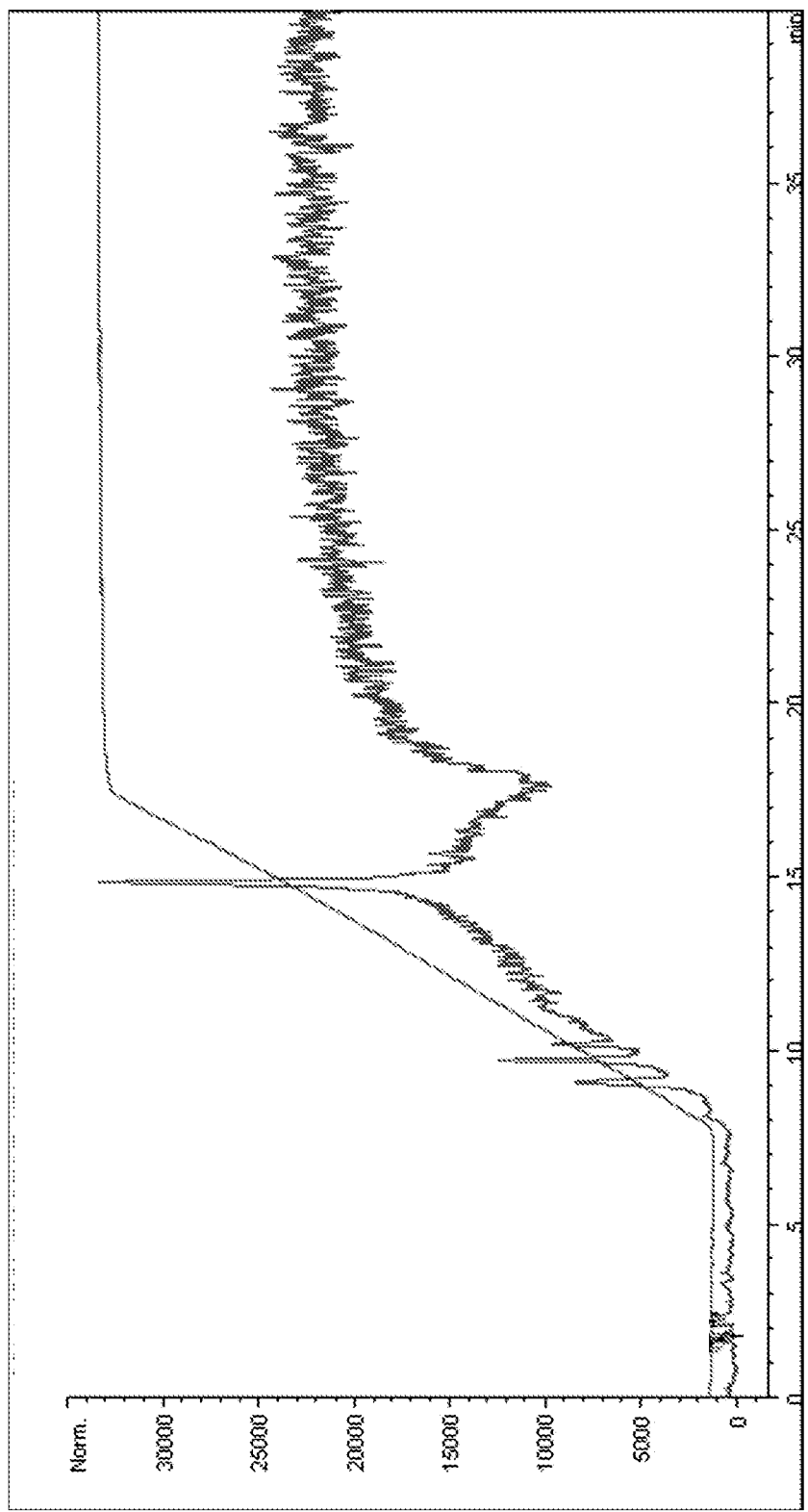
FIG. 1 is a HPLC tracing illustrating an omental lipid extract profile generated by the disclosed omental lipid extraction including performing omental lipid extraction at 200 degrees F. The x axis is time (minutes) and the y axis is the number of particles counted by the detector at a given time on the x-axis and the area under the peaks shows time and intensity of the various components of the omental extract.
Figure 2:
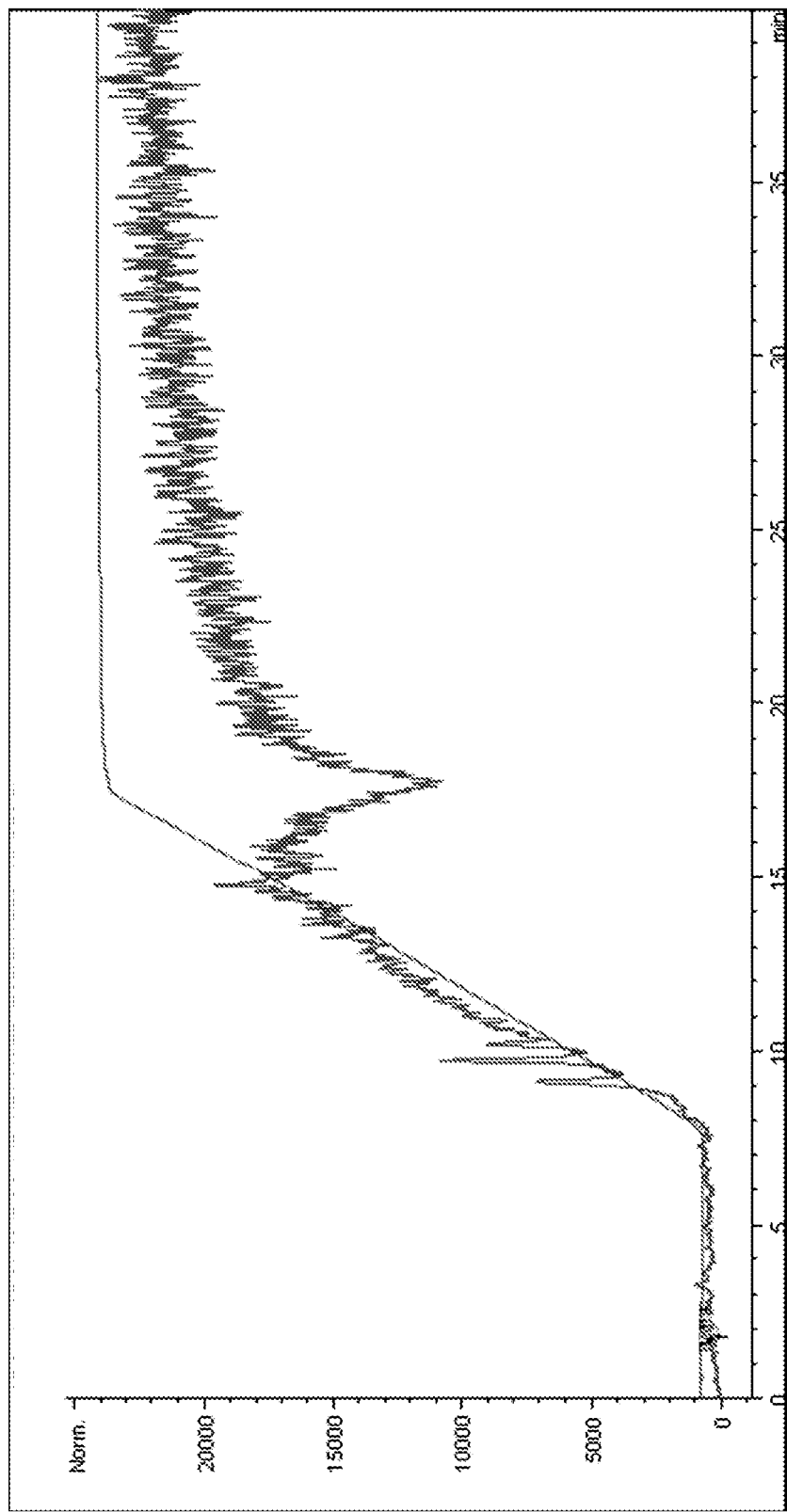
FIG. 2 is a HPLC tracing illustrating an omental lipid extract profile generated by the disclosed omental lipid extraction including performing omental lipid extraction at 210 degrees F. The x axis is time (minutes) and the y axis is the number of particles counted by the detector at a given time on the x-axis and the area under the peaks shows time and intensity of the various components of the omental extract.
Figure 3:
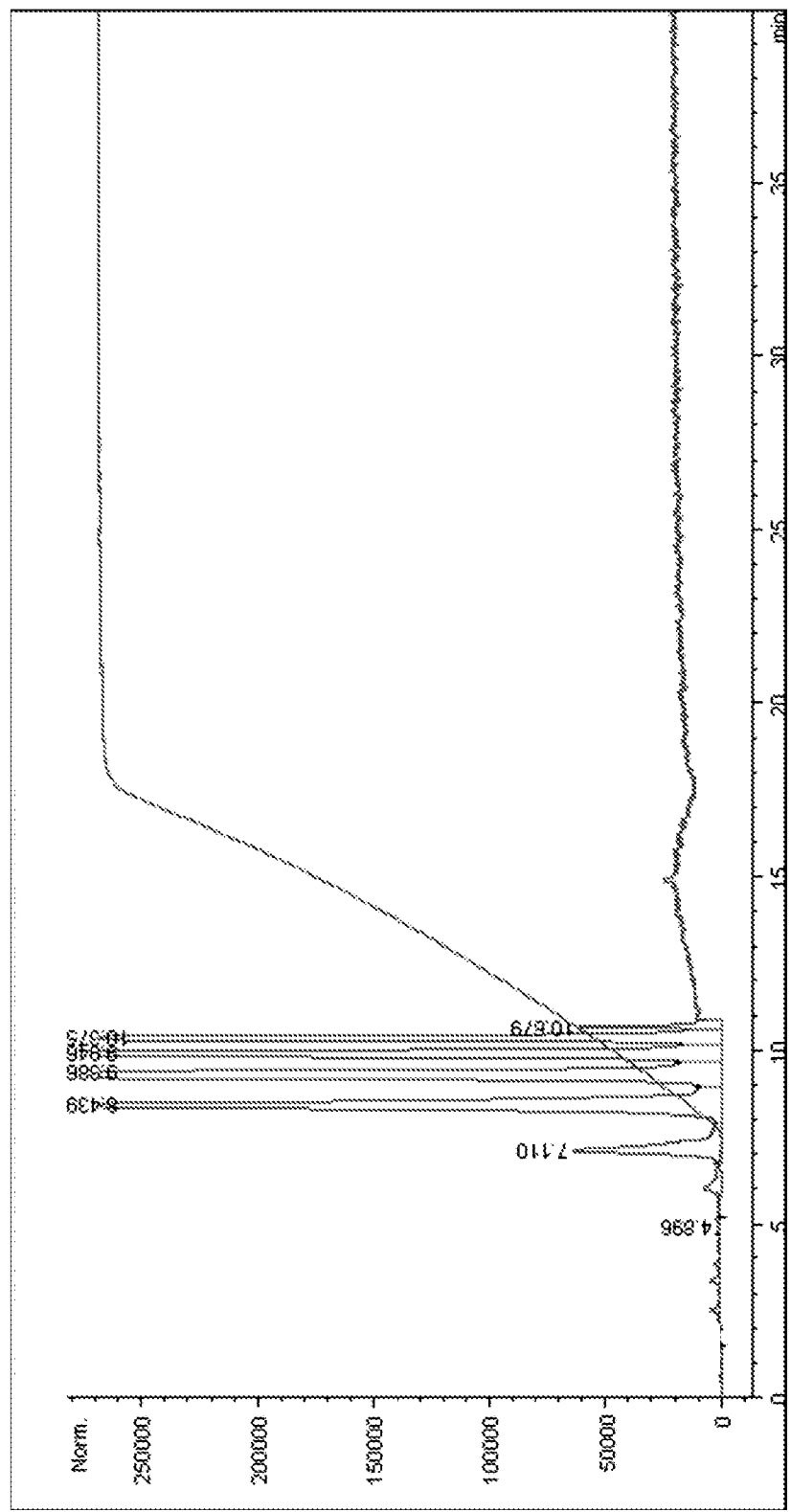
FIG. 3 is a HPLC tracing illustrating an omental lipid extract profile generated by the disclosed omental lipid extraction including performing omental lipid extraction at 225 degrees F. The x axis is time (minutes) and the y axis is the number of particles counted by the detector at a given time on the x-axis and the area under the peaks shows time and intensity of the various components of the omental extract.
Figure 4:
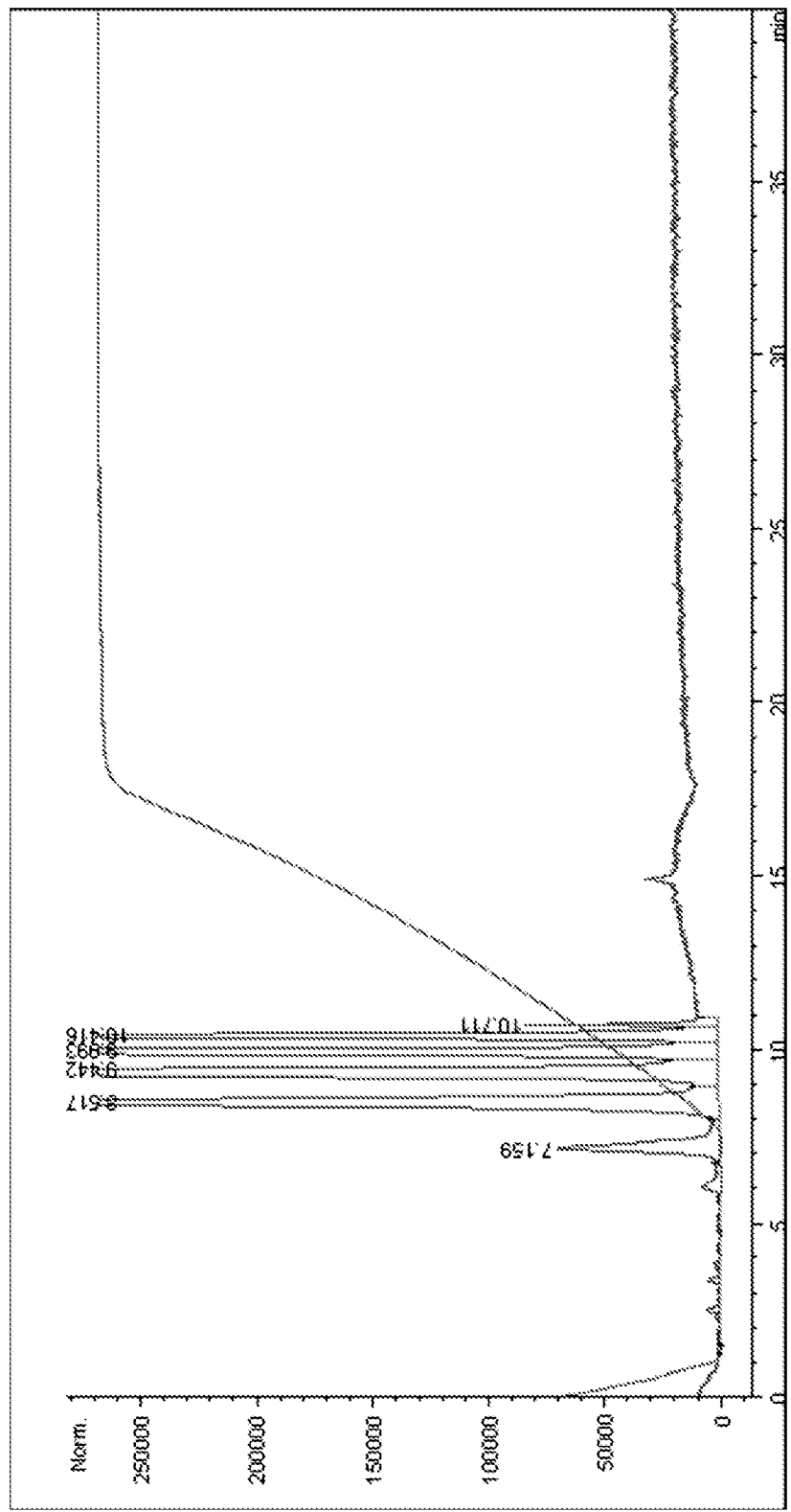
FIG. 4 is a HPLC tracing illustrating an omental lipid extract profile generated by the disclosed omental lipid extraction including performing omental lipid extraction 250 degrees F. The x axis is time (minutes) and the y axis is the number of particles counted by the detector at a given time on the x-axis and the area under the peaks shows time and intensity of the various components of the omental extract.

Mammalian omentum is known for its medicinal value, particularly its angiogenic characteristics to stimulate and enhance blood vessel and tissue growth. The therapeutic characteristics from omentum are believed to arise from the presence of therapeutic lipids in the material, as explained above.

It has surprisingly been discovered that a process that does not use a conventional organic solvent extraction process, but instead comprises a heat extraction process where the omental lipids are extracted at a temperature in the range of 210 to 240 degrees Fahrenheit, results in an end product that has a lipid profile that will be therapeutic. This omental end product may be combined by conventional techniques with various delivery vehicles, such as in a cream, ointment, lotion, gel, paste, spray or stick and so used to administer the therapeutic omental material to a subject in need of angiogenic treatment to either treat a condition that would benefit from angiogenesis, or as a preventative measure in advance of exposure to an insult that is likely to cause a condition that would benefit from angiogenesis, such as a pre-sun exposure lotion. In some examples, the omental end product may be used for cosmetic purposes in addition to or instead of therapeutic purposes. In some examples, the omental end product is directly administered without the aid of a delivery vehicle.

The omental extract or composition may be administered to treat any condition that would benefit from angiogenesis, such as conditions that are present or manifested on the surface of the skin, such as cuts, scrapes, bruises, sores, burns, abrasions, dry skin, cracked skin, chapped lips, calluses, stretch marks, wrinkles, skin infections, hemorrhoids, rashes, keratosis, seborrhea, and dandruff. In some embodiments, the omental extract or composition is used to promote hair growth and/or reduce or prevent hair loss, such as in subjects exhibiting common baldness patterns. The omentum extract or composition may also be applied to an internal area of the body for stimulating blood vessel and tissue growth in tendons, cartilage, nerves, and ligaments. Ingestion of the extract or composition may also be helpful in treating internal conditions, such as ulcers. The omentum extract may of course also be combined with pharmaceutical delivery vehicles for administration to a subject in need thereof as well as with additional therapeutic components to treat a subject's conditions, such as Alzheimer's, Parkinson's disease and/or cerebral palsy.

II. Terms

Unless otherwise noted, technical terms are used according to conventional usage. Definitions of common terms in molecular biology may be found in Benjamin Lewin, *Genes IX*, published by Jones and Bartlett Publishers, 2007 (ISBN 0763740632); Kendrew et al. (eds.), *The Encyclopedia of Molecular Biology*, published by Blackwell Science Inc., 1998; and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Administration: To provide or give a subject an agent, such as a composition that includes a disclosed omentum lipid extract by any effective route. Exemplary routes of administration include, but are not limited to, topical, injection (such as subcutaneous, intramuscular, intradermal, intraperitoneal, and intravenous), sublingual, transdermal, intranasal, and inhalation routes.

Alopecia: Hair loss (e.g., baldness or hair thinning) from one or more areas where hair is normally present. It is intended that the term encompass hair loss that results from any cause. In some examples, the term refers to the loss of scalp hair, although it is not intended to be so limited. Indeed, it is intended that the term encompass full or partial hair loss, shedding, or any decrease in the number of follicles or follicles in the anagen phase at any body site where hair is normally present.

Angiogenesis: A physiological process involving the growth of new blood vessels from pre-existing vessels. Angiogenesis can occur under normal physiological conditions such as during growth and development or wound healing (known as physiological angiogenesis) as well as pathological conditions such as in the transition of tumors from a dormant state to a malignant state (known as pathological angiogenesis). The complex phenomenon of angiogenesis begins with degradation of the basement membrane by cellular proteases. This allows endothelial cells to penetrate and migrate (process known as cell motility) into the extracellular matrix and then proliferate. In the final stages of this process, the endothelial cells align themselves to form capillary or tubelike structures (process known as tube formation). These new structures then form a network that undergoes significant remodeling and rearrangement before fully functioning capillaries exist. Therefore, angiogenesis can be studied or identified by monitoring tube formation, cell motility, and/or cell proliferation. In some examples, a disclosed omentum extract is administered to increase or induce angiogenesis, such as to increase or induce one or more activities associated with angiogenesis (e.g., cell proliferation and migration, increased vascular perfusion, accelerated wound healing, increased cell survival).

Endothelial cell: Cells that line the interior surface of blood vessels, forming an interface between circulating blood in the lumen and the rest of the vessel wall. For example, endothelial cells line the entire circulatory system. Further, both blood and lymphatic capillaries are composed of a single layer of endothelial cells.

Enhancing: To increase the quality, amount, or strength of something. In some examples, enhancing can include inducing a certain activity or effect. In one example, a disclosed omentum lipid extract enhances or induces angiogenesis or one or more activities associated with angiogenesis, for example as compared to the response in the absence of the extract. In a particular example, a disclosed composition enhances or induces angiogenesis by at least 10%, at least 20%, at least 50%, at least 70%, or even at least 90%. Such enhancement can be measured using methods disclosed herein as well as those known to one of ordinary skill in the art.

Hair: The specialized keratinized structures derived or protruding from invaginations of the epidermis that are observed on animals, including mammals. Thus, the term is also intended to encompass hair coats (e.g., fur) of various non-human animals.

Hair loss: A net decrease in the amount of hair present on a particular region (e.g., on the scalp or over the entire body) of a subject as compared to another (e.g., control) time point for the same subject or as compared to a second subject or to a population that serves as a control (i.e., a substantially unchanged standard). Hair loss need not have any particular cause, but may arise, for example, when lost hairs (e.g., shedding and/or breaking hairs) exceed the growth of new hairs. Hair loss may occur prior to any observable symptoms (e.g., baldness, bald patches or visible hair thinning). Hair loss can be quantified as at least 2%, at least 5%, at least 10%, at least 25%, at least 50%, at least 75% or up to 100% fewer hairs present on a particular region of a subject as compared to control.

Inhibiting or reducing hair loss: Inhibiting (for example, reducing or preventing) hair loss includes one or more processes associated with hair loss, such as inhibiting hair loss in a subject exhibiting common baldness patterns. Preventing hair loss refers to an intervention that ameliorates a sign or symptom of hair loss. Preventing includes prophylaxis to delay the onset of one or more processes associated with hair loss. Prevention or inhibition of hair loss does not require a total absence of hair loss. In a particular example, a disclosed composition decreases or delays a process associated with hair loss by at least 10%, at least 20%, at least 50%, or even at least 90%. Such decreases can be measured using the methods disclosed herein as well as those known in the art.

Mammal: This term includes both human and non-human mammals. Examples of mammals include, but are not limited to: humans and veterinary and laboratory animals, such as pigs, cows, goats, cats, dogs, rabbits and mice.

New Hair Growth: A term used to describe new hair grown in balding areas genetically programmed for hair follicles, as opposed to lengthening already grown hair.

Omentum: A nutrient-rich sheet of fat that is attached to the stomach and transverse colon area of most, if not all mammals (this includes feline, bovine, ovine and porcine omentum). In general, the greater omentum hangs down over the intestines in the abdominal cavity while the lesser omentum is attached to the top edge of the stomach and stretches to the underside of the liver. Omental lipid material is known to possess angiogenic factors that induce or increase angiogenesis. An "omentum extract" can be a material, such as lipids, obtained by extracting omentum according to any extraction method known to one of skill in the art, so long as it has the desired activity (e.g., angiogenic activity). In an example, an omentum lipid extract is a liquid portion of a mammalian omentum extracted when the omentum is heated to a temperature of between 210 and 240 degrees Fahrenheit and has the ability to enhance or induce angiogenesis, such as, but not limited to, an extract with an HPLC lipid profile illustrated in any one of FIGS. 1-4 obtained as described in Examples 1-3 or in FIGS. 6-7 prepared as described in Example 5. In one example, an omentum extract is one in which omentum lipids are extracted in the absence of an organic solvent.

Pharmaceutically Acceptable Vehicles: The pharmaceutically acceptable vehicles (carriers) useful in this disclosure are conventional. *Remington's Pharmaceutical Sciences*, by E. W. Martin, Mack Publishing Co., Easton, Pa., 19th Edition (1995), describes compositions and formulations suitable for pharmaceutical delivery of one or more compositions, such as one or more omentum compositions, and additional pharmaceutical agents.

In general, the nature of the vehicle will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In addition to biologically-neutral vehicles, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Symptom and sign: Any subjective evidence of disease or of a subject's condition, e.g., such evidence as perceived by the subject; a noticeable change in a subject's condition indicative of some bodily or mental state. A "sign" is any abnormality indicative of disease, discoverable on examination or assessment of a subject. A sign is generally an objective indication of disease or condition. Signs include, but are not limited to any measurable parameters such as appearance of skin, hair loss, or other indicators of a need for angiogenesis. In one example, reducing or inhibiting one or more symptoms or signs associated with alopecia, includes increasing hair growth by a desired amount, for example by at least 20%, at least 50%, at least 60%, at least 70%, at least 80%, at least 90%, at least 95%, at least 98%, or even at least 100%, as compared to the hair growth in the absence of the omentum lipid extract.

Subject: Living multi-cellular vertebrate organisms, a category that includes both human and veterinary subjects.

Therapeutically Effective Amount: An amount of a composition that alone, or together with an additional agent(s) (for example additional angiogenic factors), induces the desired response (e.g., induces or enhances angiogenesis). The preparations disclosed herein can be administered in therapeutically effective amounts.

In one example, a desired response is to induce or enhance activities associated with angiogenesis (such as endothelial proliferation, migration, and new blood vessel growth) in a subject to whom the composition is administered. An increase in such activities can be an at least 10% increase in one or more processes associated with angiogenesis, such as an at least 20%, at least 30%, at least 40%, at least 50%, at least 60%, at least 70%, at least 80%, at least 100% increase or more (e.g., a 10%, a 20%, a 30%, a 40%, a 50%, a 60%, a 70%, a 80%, a 90%, a 95%, a 100% increase). A therapeutically effective amount of a disclosed omentum extract or composition can be administered in a single dose, or in several doses, for example daily, during a course of treatment. However, the therapeutically effective amount can depend on the subject being treated, the severity and type of the condition being treated, and the manner of administration. For example, a therapeutically effective amount of such agent can vary from at least 5% omentum lipid extract prepared by the disclosed method, including about 5% to about 95% (such as 10% to 80%, 20% to 70%, 30% to 60%, 40% to 50%, including 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 97%, 98%, 99%, 100%) of omentum lipid extract daily if administered topically.

Treatment: This term refers to a therapeutic intervention that ameliorates a sign or symptom of a disease or condition, such as a condition that would benefit from angiogenesis (e.g., conditions that are present or manifested on the surface of the skin, such as cuts, scrapes, bruises, sores, burns, abrasions, dry skin, cracked skin, chapped lips, calluses, stretch marks, decubitus ulcers, wrinkles, skin infections, hemorrhoids, rashes, keratosis, seborrhea, and dandruff; cancer, such as thoracic wall cancer; sterna wounds; esophagogastrostomia; breast neoplasia; enteric fistula; ulcers; Alzheimer's; Parkinson's disease; cerebral palsy; stroke; during neurosurgery or reconstructive surgery). In some embodiments, treatment includes intervention that that ameliorates a condition associated with hair loss, such as in subjects exhibiting common baldness patterns. Treatment can also include intervention that stimulates blood vessel and tissue growth in tendons, cartilage, nerves, and ligaments. Treatment can also include action that ameliorates one or more signs and symptoms associated with an internal condition, such as an ulcer. Treatment can also induce remission or cure of a condition, such as cancer. In particular examples, treatment includes preventing a disease, for example by inhibiting the full development of a disease. Prevention of a disease does not require a total absence of disease. For example, a decrease of at least 10%, such as at least 20%, at least 30%, at least 40%, at least 50% can be sufficient.

Under conditions sufficient for: A phrase that is used to describe any environment that permits the desired activity. In one example, includes administering a disclosed omentum extract or composition to a subject sufficient to allow the desired activity. In particular examples, the desired activity is enhancing or increasing one or more processes associated with angiogenesis and/or inhibiting or reducing one or more processes associated with hair loss.

Unit dose: A physically discrete unit containing a predetermined quantity of an active material calculated to individually or collectively produce a desired effect, such as a therapeutic effect. A single unit dose or a plurality of unit doses can be used to provide the desired effect or activity, such as angiogenic activity. In one example, a unit dose includes a desired amount of a composition that inhibits or reduces one or more of the processes associated with hair loss.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. Although methods and materials similar or equivalent to those described herein can be used in the practice or testing of the present disclosure, suitable methods and materials are described below. In case of conflict, the present specification, including explanations of terms, will control. In addition, the materials, methods, and examples are illustrative only and not intended to be limiting.

III. Methods of Making Omental Extracts

Methods of making omental extracts are disclosed herein. In some embodiments, a method of making an omental extract includes heating the mammalian omentum to a temperature of between 90 and 290 and extracting the liquid portion of the heated mammelian omentum. For example, the omentum sample is heated between a temperature range between 90 degrees Fahrenheit and 290 degrees Fahrenheit, such as 90 degrees Fahrenheit and 290 degrees Fahrenheit, such as 110 degrees Fahrenheit and 280 degrees Fahrenheit, 130 degrees Fahrenheit and 270 degrees Fahrenheit, 150 degrees Fahrenheit and 270 degrees Fahrenheit, 170 degrees Fahrenheit and 270 degrees Fahrenheit, 180 degrees Fahrenheit and 270 degrees Fahrenheit, 190 degrees Fahrenheit and 270 degrees Fahrenheit, 200 degrees Fahrenheit and 270 degrees Fahrenheit, 220 degrees Fahrenheit and 250 degrees Fahrenheit, including about 195 degrees Fahrenheit, 200 degrees Fahrenheit, 205 degrees Fahrenheit, 210 degrees Fahrenheit, 211 degrees Fahrenheit, 212 degrees Fahrenheit, 213 degrees Fahrenheit, 214 degrees Fahrenheit, 215 degrees Fahrenheit, 216 degrees Fahrenheit, 217 degrees Fahrenheit, 218 degrees Fahrenheit, 219 degrees Fahrenheit, 220 degrees Fahrenheit, 221 degrees Fahrenheit, 222 degrees Fahrenheit, 223 degrees Fahrenheit, 224 degrees Fahrenheit, 225 degrees Fahrenheit, 226 degrees Fahrenheit, 227 degrees Fahrenheit, 228 degrees Fahrenheit, 229 degrees Fahrenheit, 230 degrees Fahrenheit, 231 degrees Fahrenheit, 232 degrees Fahrenheit, 233 degrees Fahrenheit, 234 degrees Fahrenheit, 235 degrees Fahrenheit, 236 degrees Fahrenheit, 237 degrees Fahrenheit, 238 degrees Fahrenheit, 239 degrees Fahrenheit, 240 degrees Fahrenheit, 241 degrees Fahrenheit, 242 degrees Fahrenheit, 243 degrees Fahrenheit, 244 degrees Fahrenheit, 245 degrees Fahrenheit, 246 degrees Fahrenheit, 247 degrees Fahrenheit, 248 degrees Fahrenheit, 249 degrees Fahrenheit, 250 degrees Fahrenheit, 251 degrees Fahrenheit, 252 degrees Fahrenheit, 253 degrees Fahrenheit, 254 degrees Fahrenheit, 255 degrees Fahrenheit, 256 degrees Fahrenheit, 257 degrees Fahrenheit, 258 degrees Fahrenheit, 259 degrees Fahrenheit, 260 degrees Fahrenheit, 261 degrees Fahrenheit, 262 degrees Fahrenheit, 263 degrees Fahrenheit, 264 degrees Fahrenheit, 265 degrees Fahrenheit, 266 degrees Fahrenheit, 267 degrees Fahrenheit, 268 degrees Fahrenheit, 269 degrees Fahrenheit, 270 degrees Fahrenheit, 275 degrees Fahrenheit and 280 degrees Fahrenheit. In some examples, the method includes heating the omentum preparation from room temperature (for example, 60 to 80 degrees Fahrenheit) to the desired final temperature, such as between 200 degrees Fahrenheit and 240 degrees Fahrenheit, including between about 210 degrees Fahrenheit and about 230 degrees, 212 degrees Fahrenheit to 225 degrees Fahrenheit, 215 degrees Fahrenheit to 225 degrees Fahrenheit, 215 degrees Fahrenheit to 220 degrees Fahrenheit, or 218 degrees Fahrenheit to 222 degrees Fahrenheit, wherein the total heating time takes approximately 2.5 hours to 4 hours, such as between 3 hours and 3.5 hours (not under vacuum). As the omental material is heated, a liquid forms, for example, a liquid oil. In some embodiments, solids are removed from the liquid oil. For example, solids may be continuously removed from the top of the liquid oil mixture. The omental material is heated to the desired temperature and water in the material is substantially removed (which can be visually determined by the lack of steam emanating from the material). In some embodiments, omentum lipids are heat extracted as described in any one of Examples 1-3 and 5.

In some embodiments, the disclosed method further includes preparing omentum for lipid extraction prior to heat extraction. For example, preparing omentum for lipid extraction includes isolating omentum from a subject and/or freezing the isolated omentum. It is contemplated that omentum can be obtained from any mammal, including, but not limited to, feline, porcine, or bovine. In one particular example, omentum is porcine omentum. In some examples, preparing omentum includes soaking omentum in a cleaning solution, such as a saline solution to remove undesired material (such as excess blood and non-omental tissue) from the omentum. For example, prior to heat extraction an omentum sample is soaked in a container, such as a coffin filter, in an about 2% to 4% saline solution (such as a 2.5% saline solution) for a period of about 24 to about 48 hours (such as 24 hours, 36 hours or 48 hours). In one particular embodiment, omentum is prepared as described in Example 1. In one embodiment, omentum is prepared as described in Examples 1-3. In another embodiment, omentum is prepared as described in Example 5.

In some embodiments, the method of extracting omentum lipids further includes purifying the oil resulting from heating the omental material, such as by filtering the yielded oil through a series of filters to remove solid omentum material. In some examples, a filter press is used to remove omentum material, such as described in Example 5. For example, a series of 13⅝ inches diameter, 22 micron pore size filter discs are used to remove solid omentum material.

The produced extract can be used as a therapeutic and/or cosmetic composition in its raw state. However, it can also be combined with a delivery vehicle and with other therapeutic agents for administration to a subject in need.

IV. Omental Lipid Extracts

Disclosed herein are omental lipid extracts derived from omental lipid extract extracted from mammalian omentum in the temperature range between 90 degrees Fahrenheit and 290 degrees Fahrenheit, such as 110 degrees Fahrenheit and 280 degrees Fahrenheit, 130 degrees Fahrenheit and 270 degrees Fahrenheit, 150 degrees Fahrenheit and 270 degrees Fahrenheit, 170 degrees Fahrenheit and 270 degrees Fahrenheit, 180 degrees Fahrenheit and 270 degrees, 190 degrees Fahrenheit and 270 degrees Fahrenheit, 200 degrees Fahrenheit and 270 degrees Fahrenheit, 220 degrees Fahrenheit and 250 degrees Fahrenheit, including about 195 degrees Fahrenheit, 200 degrees Fahrenheit, 205 degrees Fahrenheit, 210 degrees Fahrenheit, 215 degrees Fahrenheit, 220 degrees Fahrenheit, 221 degrees Fahrenheit, 222 degrees Fahrenheit, 223 degrees Fahrenheit, 224 degrees Fahrenheit, 225 degrees Fahrenheit, 226 degrees Fahrenheit, 227 degrees Fahrenheit, 228 degrees Fahrenheit, 229 degrees Fahrenheit, 230 degrees Fahrenheit, 231 degrees Fahrenheit, 232 degrees Fahrenheit, 233 degrees Fahrenheit, 234 degrees Fahrenheit, 235 degrees Fahrenheit, 236 degrees Fahrenheit, 237 degrees Fahrenheit, 238 degrees Fahrenheit, 239 degrees Fahrenheit, 240 degrees Fahrenheit, 241 degrees Fahrenheit, 242 degrees Fahrenheit, 243 degrees Fahrenheit, 244 degrees Fahrenheit, 245 degrees Fahrenheit, 246 degrees Fahrenheit, 247 degrees Fahrenheit, 248 degrees Fahrenheit, 249 degrees Fahrenheit, 250 degrees Fahrenheit, 251 degrees Fahrenheit, 252 degrees Fahrenheit, 253 degrees Fahrenheit, 254 degrees Fahrenheit, 255 degrees Fahrenheit, 256 degrees Fahrenheit, 257 degrees Fahrenheit, 258 degrees Fahrenheit, 259 degrees Fahrenheit, 260 degrees Fahrenheit, 261 degrees Fahrenheit, 262 degrees Fahrenheit, 263 degrees Fahrenheit, 264 degrees Fahrenheit, 265 degrees Fahrenheit, 266 degrees Fahrenheit, 267 degrees Fahrenheit, 268 degrees Fahrenheit, 269 degrees Fahrenheit, 270 degrees Fahrenheit, 275 degrees Fahrenheit and 280 degrees Fahrenheit.

Figure 6:
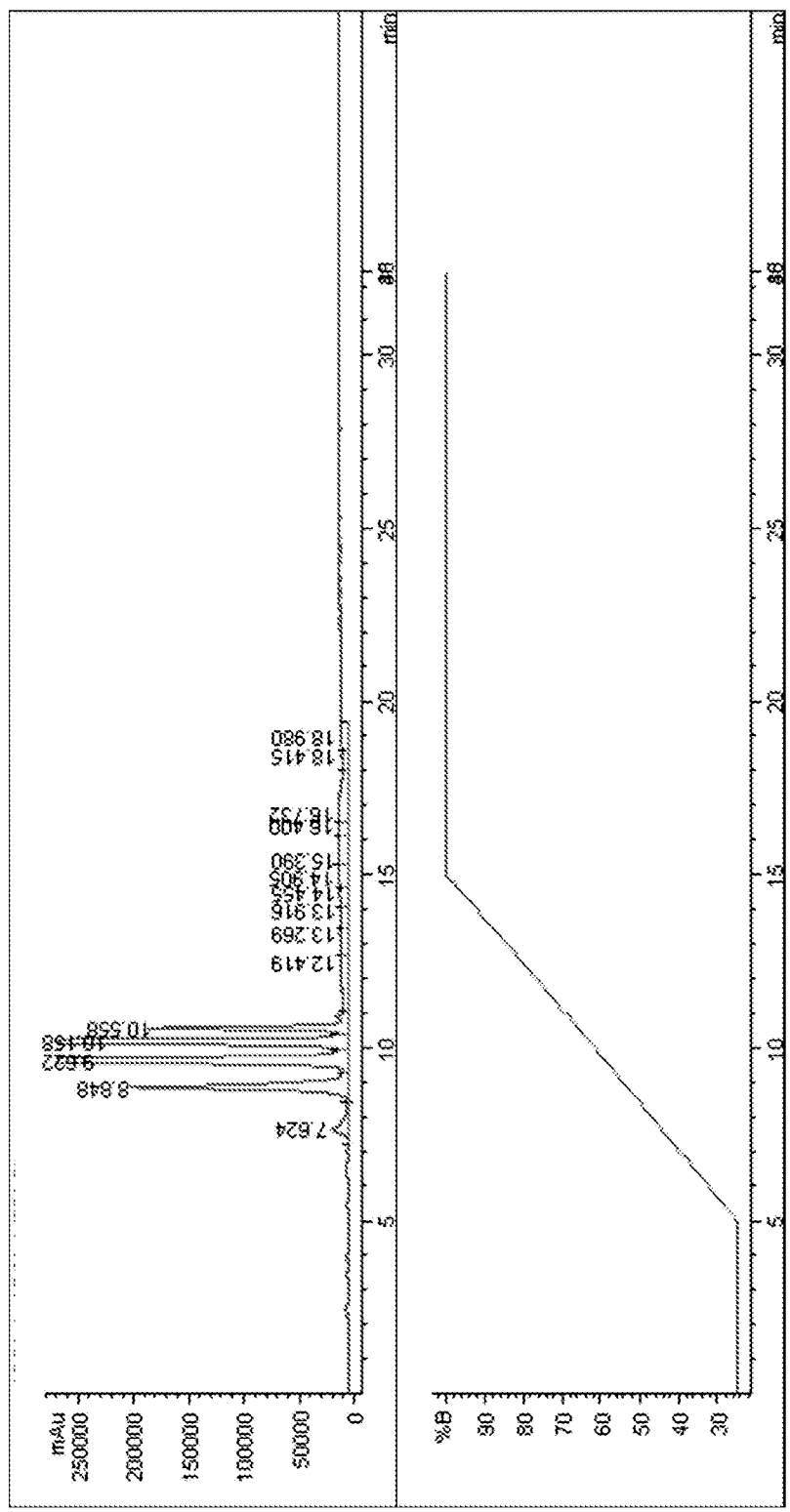
FIG. 6 is a HPLC tracing illustrating an omental lipid extract profile generated by the disclosed omental lipid extraction as described in Example 5. The x axis is time (minutes) and the y axis is mAu and the area under the peaks shows time and intensity of the various components of the omental extract.
Figure 7:
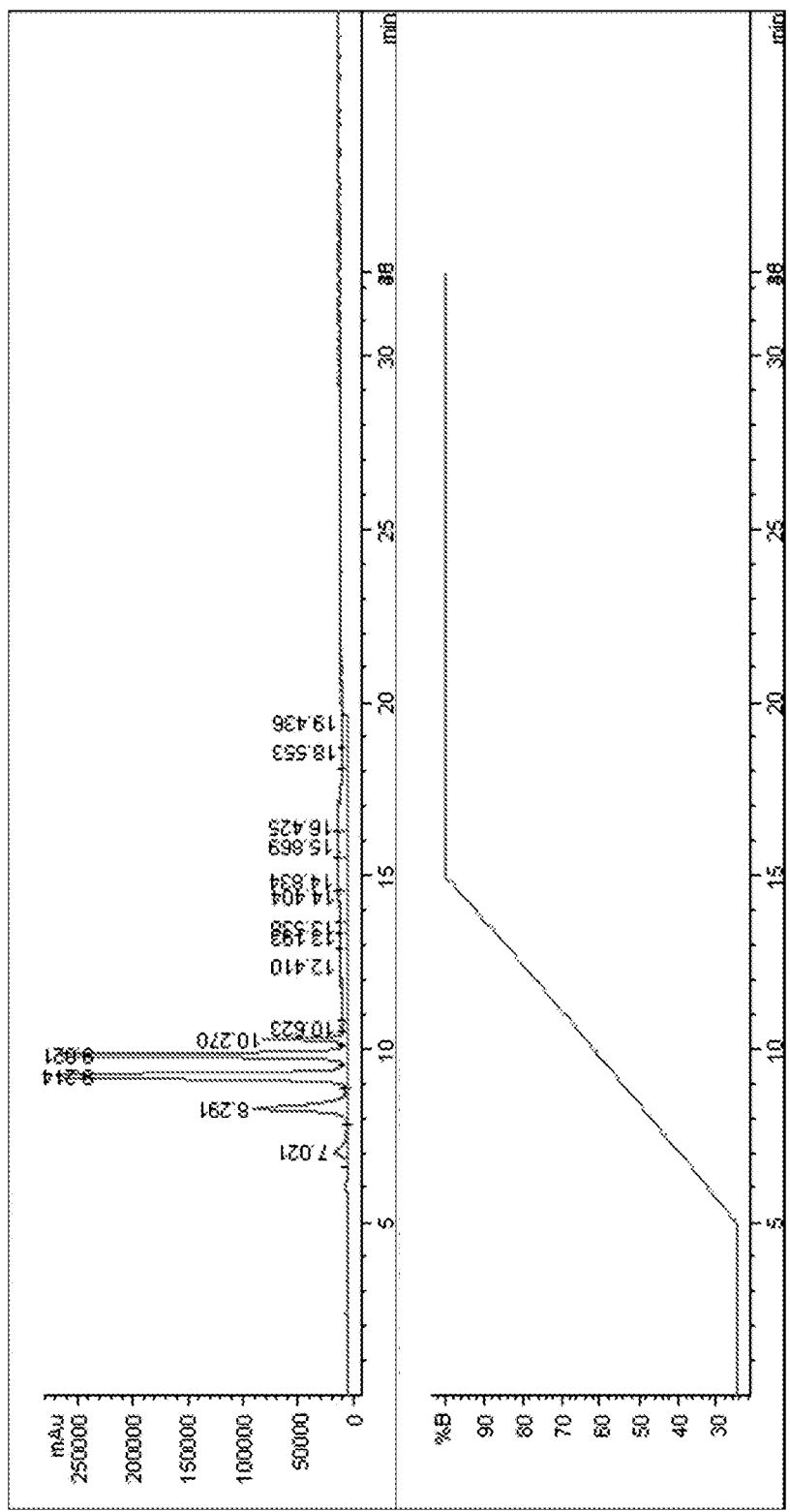
FIG. 7 is a HPLC tracing illustrating an omental lipid extract profile generated by a disclosed omental lipid extraction as described in Example 5. The x axis is time (minutes) and the y axis is mAu and the area under the peaks shows time and intensity of the various components of the omental extract.

In one particular example, the composition includes omentum lipid extract extracted from mammalian omentum, such as porcine omentum between 210 and 240 degrees Fahrenheit, such as in Example 3 or Example 5. In some disclosed embodiments, the composition includes an omentum lipid extract with an HPLC lipid profile as illustrated in FIGS. 1-4 and described in Examples 1-3. In some disclosed embodiments, the composition includes an omentum lipid extract with an HPLC lipid profile as illustrated in FIG. 6 or 7 and prepared as described in Example 5.

V. Compositions with Biological Activity

Disclosed herein are omentum lipid compositions with biological activity, including, but not limited to, angiogenic, skin-improving, hair growth promoting activity or any combination thereof. In some embodiments, a composition includes an omental lipid extract extracted from mammalian omentum in the temperature range between 190 degrees Fahrenheit and 280 degrees Fahrenheit, such as 200 degrees Fahrenheit and 270 degrees Fahrenheit, 210 degrees Fahrenheit and 240 degrees Fahrenheit, including about 195 degrees Fahrenheit, 200 degrees Fahrenheit, 205 degrees Fahrenheit, 210 degrees Fahrenheit, 211 degrees Fahrenheit, 212 degrees Fahrenheit, 213 degrees Fahrenheit, 214 degrees Fahrenheit, 215 degrees Fahrenheit, 216 degrees Fahrenheit, 217 degrees Fahrenheit, 218 degrees Fahrenheit, 219 degrees Fahrenheit, 220 degrees Fahrenheit, 221 degrees Fahrenheit, 222 degrees Fahrenheit, 223 degrees Fahrenheit, 224 degrees Fahrenheit, 225 degrees Fahrenheit, 226 degrees Fahrenheit, 227 degrees Fahrenheit, 228 degrees Fahrenheit, 229 degrees Fahrenheit, 230 degrees Fahrenheit, 231 degrees Fahrenheit, 232 degrees Fahrenheit, 233 degrees Fahrenheit, 234 degrees Fahrenheit, 235 degrees Fahrenheit, 236 degrees Fahrenheit, 237 degrees Fahrenheit, 238 degrees Fahrenheit, 239 degrees Fahrenheit, 240 degrees Fahrenheit, 241 degrees Fahrenheit, 242 degrees Fahrenheit, 243 degrees Fahrenheit, 244 degrees Fahrenheit, 245 degrees Fahrenheit, 246 degrees Fahrenheit, 247 degrees Fahrenheit, 248 degrees Fahrenheit, 249 degrees Fahrenheit, 250 degrees Fahrenheit, 251 degrees Fahrenheit, 252 degrees Fahrenheit, 253 degrees Fahrenheit, 254 degrees Fahrenheit, 255 degrees Fahrenheit, 256 degrees Fahrenheit, 257 degrees Fahrenheit, 258 degrees Fahrenheit, 259 degrees Fahrenheit, 260 degrees Fahrenheit, 261 degrees Fahrenheit, 262 degrees Fahrenheit, 263 degrees Fahrenheit, 264 degrees Fahrenheit, 265 degrees Fahrenheit, 266 degrees Fahrenheit, 267 degrees Fahrenheit, 268 degrees Fahrenheit, 269 degrees Fahrenheit, 270 degrees Fahrenheit, 275 degrees Fahrenheit and 280 degrees Fahrenheit.

In one particular example, the composition includes omentum lipid extract extracted from mammalian omentum, such as porcine omentum, between 210 degrees Fahrenheit and 240 degrees Fahrenheit, such as in Example 3 or Example 5. In some disclosed embodiments, the composition includes an omentum lipid extract with an HPLC lipid profile as illustrated in any one of FIGS. 1-4 and prepared as described in Examples 1-3. In some disclosed embodiments, the composition includes an omentum lipid extract with an HPLC lipid profile as illustrated in FIG. 6 or 7 and prepared as described in Example 5.

VI. Additional Substances in Compositions and Extracts

The disclosed compositions or extracts can contain additional substances that are customarily used in cosmetics, for example, perfume; antimicrobial agents; antibacterial agents; refatting agents; complexing and sequestering agents; pearlescent agents; plant extracts; vitamins, such as retinol or vitamin C; active agents; preservatives; bactericides; surfactants, dyes, colorants, pigments, or any substances which have a coloring effect; emulsifiers; thickeners; softening, moisturizing, and/or humectant substances; or other common constituents of a cosmetic or dermatological formulation, such as alcohols, polyols, polymers, foam stabilizers, electrolytes, organic solvents, or silicone derivatives. The compositions can also comprise functional additives such as keratolytic agents, oxidizers, sun-protection agents, and skin smoothing agents. The compositions may also contain components that are considered beneficial in mesotherapy injectional treatment of the skin and underlying subcutaneous tissue, including antioxidants, such as dimethylaminoethanol, alpha lipoic acid, and ascorbic acid. Agents that may enhance the efficacy of the compositions or extracts, such as lipophilic and lipophobic penetration enhancers (e.g., triethyl citrate, propylene glycol, fatty acid esters and others) may also be included in the compositions. Agents that may provide additional enhancement to the vascular perfusion of the skin, such as aminophyllin, or pentoxifylline may also be included in the compositions. Agents that may enhance the turgor and tonicity of the skin as well as allow for the contraction or shrinkage of the underlying subcutaneous tissue structure, such as phosphatidyl choline and deoxycholate sulfate may also be included in the compositions. Physiologic substances that may provide hormonal benefit, such as substances of estrogenic or testosterrogenic stimulus to the skin, including estriol, and testosterone may also be included in the compositions.

The disclosed omentum lipid extracts or compositions can include one or more preservatives. These preservatives include, for example, Opthiphen™ (from International Specialty Products), Geogard® Ultra (from Lonza), preservatives listed in the European Union Cosmetic Directive and others, such as formaldehyde donors (such as, for example, DMDM hydatoin, which is available under the trade name GLYDAN® from Lonza), iodopropyl butylcarbamates (for example, those which are available under the trade names GLYCACIL-S™ from LONZA™ and/or DEKABEN LMB™ from Jan Dekker), parabens (for example, alkyl esters of the p-hydroxybenzoic acid, such as methyl-, ethyl-, propyl-, and/or butylparaben), phenoxyethanol, ethanol, benzoic acid, and salicylic acid. The preservation system can further include preservative auxiliaries, such as octoxyglycerin or glycine soya. Other preservatives or preservative auxiliaries include dibromocyanobutane (2-bromo-2-bromomethylglutarodinitrile), 3-iodo-2-propynyl butylcarbamate, 2-bromo-2-nitropropane-1,3-diol, imidazolidinyl urea, 5-chloro-2-methyl-4-isothiazolin-3-one, 2-chloroacetamide, benzalkonium chloride, and benzyl alcohol.

The compositions can also include one or more conditioners, such as a water soluble conditioning agent. Other conditioners include, for example, compounds that are called polyquaternium in accordance with the International Nomenclature for Cosmetic Ingredients (INCI), in particular Polyquaternium-1 to Polyquaternium-56.

The compositions can be dispensed from a soft tube, a jar, a bottle, a pump, a can, a spray can or spray bottle, or from some other known container.

VII. Pharmaceutical Compositions

The disclosed omentum extracts and compositions can be useful, at least, for enhancing or promoting angiogenesis, inhibiting or reducing hair loss, increasing hair growth, improving skin quality, or any combination thereof. Accordingly, pharmaceutical compositions comprising a disclosed omentum lipid extract either alone or in combination with additional activity agents, such as sodium hyaluronate are also described herein.

Formulations for pharmaceutical compositions are well known in the art. For example, *Remington's Pharmaceutical Sciences*, by E. W. Martin, Mack Publishing Co., Easton, Pa., 19th Edition, 1995, describes exemplary formulations (and components thereof) suitable for pharmaceutical delivery of a disclosed omentum lipid extract. In some examples, the compositions also include additional agents such as sodium hyaluronate or other angiogenic agents such as VEGF. Pharmaceutical compositions comprising at least one of these compounds can be formulated for use in human or veterinary medicine. Particular formulations of a disclosed pharmaceutical composition may depend, for example, on the mode of administration (e.g., topical or parenteral) and/or on the condition to be treated (e.g., baldness, internal condition, such as ulcers or Alzheimer's). In some embodiments, formulations include a pharmaceutically acceptable carrier in addition to at least one active ingredient, such as an omentum lipid extract.

Pharmaceutically acceptable carriers useful for the disclosed methods and compositions are conventional in the art. The nature of a pharmaceutical carrier will depend on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like as a vehicle. In addition to biologically neutral carriers, pharmaceutical compositions to be administered can optionally contain minor amounts of non-toxic auxiliary substances or excipients, such as wetting or emulsifying agents, preservatives, and pH buffering agents and the like; for example, sodium acetate or sorbitan monolaurate. Other non-limiting excipients include, nonionic solubilizers, such as cremophor, or proteins, such as human serum albumin.

The disclosed pharmaceutical compositions may be formulated as a pharmaceutically acceptable salt. Pharmaceutically acceptable salts are non-toxic salts of a free base form of a compound that possesses the desired pharmacological activity of the free base. These salts may be derived from inorganic or organic acids. Non-limiting examples of suitable inorganic acids are hydrochloric acid, nitric acid, hydrobromic acid, sulfuric acid, hydriodic acid, and phosphoric acid. Non-limiting examples of suitable organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, methyl sulfonic acid, salicylic acid, formic acid, trichloroacetic acid, trifluoroacetic acid, gluconic acid, asparagic acid, aspartic acid, benzenesulfonic acid, p-toluenesulfonic acid, naphthalenesulfonic acid, and the like. Lists of other suitable pharmaceutically acceptable salts are found in *Remington's Pharmaceutical Sciences*, 19th Edition, Mack Publishing Company, Easton, Pa., 1995. A pharmaceutically acceptable salt may also serve to adjust the osmotic pressure of the composition.

The dosage form of a disclosed pharmaceutical composition will be determined by the mode of administration chosen. For example, topical forms may be employed. Methods of preparing such dosage forms are disclosed herein, or will be apparent to those skilled in the art. Dosages of the disclosed lipid extract may be determinable by those of skill in the art without more than routine experimentation and will depend upon the ailment to be treated or prevented. In some examples, a topical formulation includes at least 5% omentum lipid extract prepared by the disclosed method (such as the method described in any one of Examples 1-3 and 5), including about 5% to about 95% (such as 10% to 80%, 20% to 70%, 30% to 60%, 40% to 50%, including 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or 95%) of omentum lipid extract. The topical formulation can be administered daily, weekly, or as needed, including at least once a week, such as at least two times, at three times, at least four times, at least five times, or at least six times a week or daily.

VIII. Administration of Disclosed Extracts and Compositions

Methods of administration of any of the disclosed compositions and extracts are routine. For example, the disclosed compositions (such as those that include a composition with angiogenic activity for enhancing or inducing angiogenesis) can be administered topically, transdermally, parenterally, injection or via inhalation or spray. In a particular example, a composition is administered topically to a skin surface of a mammalian subject, such as a human.

The therapeutically effective amount of the agents administered can vary depending upon the desired effects and the subject to be treated. In one example, a therapeutically effective amount is an amount that will cover the desired area in need of treatment. In one example, the method includes daily topical administration of a formulation including at least a 5% omentum lipid extract prepared by a disclosed method (such as, but not limited to, the methods described in Example 3 or Example 5), including about 5% to about 95% (such as 10% to 80%, 20% to 70%, 30% to 60%, 40% to 50%, including 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or 95%) of omentum lipid extract.

In particular examples, the subject applies a composition (such as a disclosed omentum lipid extract) on a multiple daily dosing schedule, such as at least two consecutive days, 10 consecutive days, and so forth, for example for a period of weeks, months, or years. In one example, the subject applies the composition (such as a disclosed omentum lipid extract) topically daily for a period of at least 7 days, such as at least 14 days, at least 30 days, such as at least 2 months, at least 4 months, at least 6 months, at least 12 months, at least 24 months, or at least 36 months. The composition applied might be applied once, twice, or three times a day or more often. The amount applied in each dosing may be an amount sufficient to cover the area in which treatment is desired, which might be for example, 4-5 milliliters of the composition, but which will of course depend on the area to be treated and the desired dosage.

The therapeutic compositions, such as a disclosed omentum lipid extract composition can further include one or more biologically active or inactive compounds (or both), such as additional angiogenic and/or antioxidant agents and conventional non-toxic pharmaceutically acceptable carriers, respectively. In a particular example, a therapeutic composition further includes one or more biologically inactive compounds. Examples of such biologically inactive compounds include, but are not limited to: carriers, thickeners, diluents, buffers, preservatives, and carriers. The pharmaceutically acceptable carriers useful for these formulations are conventional (see Remington's Pharmaceutical Sciences, by E. W. Martin, Mack Publishing Co., Easton, Pa., 19th Edition (1995)). In general, the nature of the carrier will depend on the particular mode of administration being employed. In addition to biologically-neutral carriers, pharmaceutical compositions to be administered can include minor amounts of non-toxic auxiliary substances, such as wetting or emulsifying agents, preservatives, and pH buffering agents and the like, for example sodium acetate or sorbitan monolaurate.

Although the present disclosure has provided a detailed description using any of the disclosed compositions and extracts for enhancing or inducing angiogenesis, such as to improve skin quality and stimulate hair growth, it is contemplated the disclosed compositions and extracts can be used to treat any disorder that could benefit from inducing or enhancing angiogenesis. For example, it is contemplated that the present extracts and compositions can be used to reduce, prevent or treat one or more signs or symptoms associated with Alzheimer's disease.

IX. Methods of Use a. Methods of Inducing or Increasing Angiogenesis

Methods of enhancing or inducing angiogenesis are disclosed. In some examples, methods of inducing or increasing angiogenesis include methods of inducing or increasing one or more activities associated with angiogenesis by applying a solution or topical ointment containing a disclosed omentum lipid extract either alone or in combination with additional active ingredients, including, but not limited to sodium hyaluronate. In one example, the solution or topical ointment includes a disclosed omentum lipid extract without additional active ingredients. In some examples, the compositions do not include vitamins A, D, E or a combination thereof. The method can be performed by a clinician or other healthcare provider. The method is also designed for home use. Compositions and kits for inducing or enhancing angiogenesis are also provided that can include a disclosed composition (including oral or topical) and one or more additional angiogenesis compositions, such as vascular endothelial growth factor (VEGF).

Any condition that would benefit from angiogenesis (e.g., conditions that are present or manifested on the surface of the skin, such as cuts, scrapes, bruises, sores, burns, abrasions, dry skin, cracked skin, chapped lips, calluses, decubitus ulcers, stretch marks, wrinkles, skin infections, hemorrhoids, rashes, keratosis, seborrhea, and dandruff; cancer, such as thoracic wall cancer; sterna wounds; esophagogastrostomia; breast neoplasia; enteric fistula; ulcers; Alzheimer's; during neurosurgery or reconstructive surgery; baldness; blood vessel and tissue growth in tendons, cartilage, nerves, and ligaments) can be treated with using the methods provided herein. Skin surfaces that can be treated include, but are not limited to, periorbits, lips, cheeks, nasolabial folds, forehead, neck, upper lip rhytides, stomach, neck, back, chest, hands, legs, feet, or any combination thereof. In an example, the skin of any facial surface can be treated using the methods provided herein. The method can be applied to any facial area and/or to any body surface area, with other exemplary areas of application being the chest and neck. More than one skin surface can be treated during the same treatment period. In a particular example, a liquid or cream form of a disclosed composition or extract is applied substantially evenly across the surface of the skin, forming a layer of the composition or extract on the skin.

Omentum lipid extract compositions and kits for inducing or enhancing angiogenesis are also disclosed herein for use in the home or by a clinician. In one example, this kit is suitable for use by a clinician or aesthetician. In such example, the kit can further include applicators to assist with applying the composition. Generally the kit also includes instructions for use. These instructions can be written or in a digital formal (such as a videotape, DVD or CD) for use with electronic devices such as computers, CD players, mp3 players or DVD players and the like. In another example, the kit is suitable for use in the home. This kit can include an applicator, such as a sponge or cloth, for applying the composition. Alternatively, one or more fingers can be used to apply the composition. Generally, the kit also includes instructions for use. These instructions can be written or in a digital format (such as a videotape, DVD or CD) for use with electronic devices such as computers, CD players, mp3 players or DVD players.

In some examples, the kit includes a disclosed composition or extract and one or more additional angiogenic compounds, antioxidants (e.g., vitamin C, vitamin E, selenium and/or beta-carotene), or combination thereof in separate containers or as a single composition in a single container. In one example, the composition or extract is applied to a target area. In one specific non-limiting example, the omentum lipid extract angiogenesis kit can be used by a person in the home as follows. First, a measured quantity of the composition or extract is applied to the area in need of angiogenesis, such as the skin, by the use of an applicator, such as a sponge or cloth, or by the use of one or more fingers, to provide an even layer of the composition or extract on the surface to be treated. The composition or extract is either allowed a certain time length to be passively absorbed into the treated surface or absorption of the composition/extract by the treated surface can be facilitated by gently rubbing the composition into the treated surface with the fingertips. Generally, normal care procedures, such as makeup application (if treating the face), shampooing (if treating the scalp) and applying additional moisturizing agents, can be resumed following application of the omentum lipid composition/extract.

This process can be performed as described twice daily, daily, every other day, bi-weekly, weekly, every other week, or monthly, or for some other interval, such as once every 3 to 5 days.

b. Methods of Improving Skin Quality

Methods of improving skin quality are disclosed. In some examples, methods of improving skin quality include methods of improving skin quality by reducing or inhibiting one or more signs associated with aging skin by applying a solution or topical ointment containing a disclosed omentum lipid extract either alone or in combination with additional active ingredients, including, but not limited to sodium hyaluronate. In one example, the solution or topical ointment includes a disclosed omentum lipid extract without additional active ingredients. In some examples, the compositions do not include vitamins A, D, E or a combination thereof. The method can be performed by a clinician or other healthcare provider. The method is also designed for home use. The method can reduce the appearance of skin changes associated with aging, visibly reduce human skin wrinkles, stimulate regeneration of skin cells, stimulate microcirculation within the skin, and improve the textural quality of skin (e.g., reduce chapping, cracking, flakiness, increase moisture content of skin, softness of skin). Compositions and kits for improving skin quality are also provided that can include a disclosed composition (including oral or topical) and one or more additional anti-aging compositions, such as sodium hyaluronate.

Any skin surface (e.g., the epidermis of the skin) can be treated with the using the methods provided herein. Skin surfaces that can be treated include, but are not limited to, periorbits, lips, cheeks, nasolabial folds, forehead, neck, upper lip rhytides, stomach, neck, back, chest, hands, legs, feet, or any combination thereof. In an example, the skin of any facial surface can be treated using the methods provided herein. The method can be applied to any facial area and/or to any body surface area, with other immediate areas of application being the chest and neck. More than one skin surface can be treated during the same treatment period. In a particular example, a liquid or cream form of a disclosed composition or extract is applied substantially evenly across the surface of the skin, forming a layer of the composition or extract on the skin.

Omentum lipid extract compositions and kits for improving skin quality are also disclosed herein for use in the home or by a clinician. In one example, this kit is suitable for use by a clinician or aesthetician. In such example, the kit can further include applicators to assist with applying the composition. Generally the kit also includes instructions for use. These instructions can be written or in a digital formal (such as a videotape, DVD or CD) for use with electronic devices such as computers, CD players, mp3 players or DVD players and the like. In another example, the kit is suitable for use in the home. This kit can include an applicator, such as a sponge or cloth, for applying the composition. Alternatively, one or more fingers can be used to apply the composition. Generally, the kit also includes instructions for use. These instructions can be written or in a digital format (such as a videotape, DVD or CD) for use with electronic devices such as computers, CD players, mp3 players or DVD players.

In some examples, the kit includes one of the disclosed compositions or extracts and one or more additional anti-aging compounds, such as antioxidants (e.g., vitamin C, vitamin E, selenium and/or beta-carotene), either in two separate containers or as a single composition in a single container. In one example, the composition or extract is applied to a target skin area. In one specific non-limiting example, the omentum lipid extract anti-aging kit can be used by a person in the home as follows. First, a measured quantity of the composition or extract is applied to the surface the skin by the use of an applicator, such as a sponge or cloth, or by the use of one or more fingers, to provide an even layer of the composition or extract on the skin surface. The composition or extract is either allowed a certain time length to be passively absorbed into the skin surface or absorption of the composition/extract by the skin surface can be facilitated by gently rubbing the composition into the skin surface with the fingertips. Generally, normal skin care procedures, such as makeup application and applying additional moisturizing agents, can be resumed following application of the omentum lipid composition/extract.

This process can be performed as described twice daily, daily, every other day, bi-weekly, weekly, every other week, or monthly, or for some other interval, such as once every 3 to 5 days. Improving skin quality includes reversing, slowing the progression of, or preventing skin changes associated with natural or innate aging. As used herein, prevent and variations thereof refer to any degree of delaying the onset of skin changes. For example, improving skin quality includes the reversal, slowing the progression of, or prevention of skin changes associated with free radical formation and activity. In one example, improving skin quality includes reversal, slowing the progression of, or prevention of skin changes associated with sun damage or photo aging-skin changes associated with exposure to sunlight or other forms of actinic radiation (for example, UV radiation and tanning booths). As another example, improving skin quality also can include reversing, slowing the progression of, or preventing skin changes resulting from extrinsic factors, including, but not limited to, radiation, air pollution, wind, cold, dampness, heat, chemicals, smoke, cigarette smoking, and combinations thereof. Improving skin quality also can include reversing, preventing or reducing scarring that can result, for example, from certain skin conditions (for example, acne), infections (for example, leishmaniasis), or injury (for example, abrasions, punctures, lacerations, or surgical wounds). Improvements to the skin can also include at least one of the following: making facial lines appear less noticeable, making facial lines and/or wrinkles feel plumped, improving the appearance of suborbital lines and/or periorbital lines, improving the appearance of crow's feet, reducing and/or diminishing the appearance of wrinkles, particularly facial wrinkles on the cheeks, forehead (for example, perpendicular wrinkles between eyes, horizontal wrinkles above the eyes), and/or around the mouth, and particularly deep wrinkles, folds, or creases, improving skin suppleness, reducing and/or eliminating fine and/or deep lines, folds and creases, and smoothing skin. Methods for measuring improved skin quality are known in the art. See, for example, U.S. Pat. Nos. 6,866,856 and 6,682,763.

Skin changes treatable by practicing the methods and using the kits disclosed herein include, for example, wrinkles (including, but not limited to, human facial wrinkles), creases, furrows, folds and fine lines, deepening of skin lines, thinning of skin, preventing or reducing scarring, yellowing of the skin, mottling, hyperpigmentation, appearance of pigmented and/or non-pigmented age spots, leatheriness, loss of elasticity, loss of recoilability, loss of collagen fibers, abnormal changes in the elastic fibers, deterioration of small blood vessels of the dermis, formation of solar increased visible vasculature on the skin surface, and combinations thereof.

Improving skin quality includes decreasing, reducing, and/or minimizing one or more of the skin changes discussed above. Improving skin quality can result in the skin having a more youthful appearance. Improving skin quality can result in the skin having a smoother, hydrated (less dry), or less scaly appearance. For example, in certain embodiments, improving skin quality can include a reduction in roughness, dryness, or scaliness. Improving skin quality includes the effacement and improvement of lines and wrinkles, improvement in turgor, and tonicity, with the observed desired effects of lifting and tightening.

The textural qualities of the skin can be improved, including softness, suppleness, and smoothness, leading to enhancement of luster, clarity and brightness. Additional and important qualities of the skin that can be subjectively and objectively measured include, but are not limited to skin laxity, or conversely skin tightness, and the presence and degree of textural fine lines and coarser lines within the skin.

These are the same qualities by which the external aspects of appearance (for example, aging of skin) are judged. Improvement in these qualities by the method of treatment and kits disclosed herein result in a benefit based on visual judgment of appearance. Changing a quality of the skin by the methods disclosed herein lessens the appearance of aging of the skin.

Desired benefits may include not only physiologic benefit to the skin, but therapeutic and pharmacologic benefits, such as possible malignancy prevention and treatment, whether by chemoprevention or enhancement of photodynamic therapy. Benefits may also include acne treatment and suppression, by including compositions which suppress sebaceous glandular activity.

c. Methods of Promoting Hair Growth and/or Inhibiting Hair Loss

Methods of promoting hair growth and/or inhibiting hair loss (including preventing or reducing hair loss) are disclosed. In some examples, methods of promoting hair growth and/or inhibiting hair loss by reducing or inhibiting one or more signs associated with hair loss by applying a solution or topical ointment containing a disclosed omentum lipid extract either alone or in combination with additional active ingredients, including, but not limited to sodium hyaluronate. In one example, the solution or topical ointment includes a disclosed omentum lipid extract without additional active ingredients.

The disclosed method of promoting hair growth and/or inhibiting hair loss can be used to treat hair loss associated with a health disorder, such as alopecia areata, traction alopecia, folliculitis alopecia, telogen effluvium, loose-anagen syndrome, toxic alopecia, acquired immune deficiency (AID), hypothroidism, hyperthyroidism, lupus erythematosus, diabetes, iron deficiency, syphilis, zinc deficiency, trichotillomania, or Cushing syndrome. The disclosed method of promoting hair growth and/or inhibiting hair loss can also be used to treat hair loss associated with a therapeutic treatment such as chemotherapy or radiation therapy.

The disclosed method can be performed by a clinician or other healthcare provider. The method is also designed for home use. The method can produce new hair growth and/or reduce, inhibit, or prevent further hair loss. Compositions and kits for promoting hair growth and/or inhibiting hair loss are also provided that can include a disclosed composition (including oral or topical) and one or more additional hair growth promoting or hair loss inhibiting compositions, such as finasteride, dutasteride and topically applied minoxidil solution.

Any balding or bald areas of skin (e.g., the epidermis of the skin) can be treated with the using the methods provided herein, including the scalp, face, extremities or genital regions. More than one skin surface can be treated during the same treatment period. In a particular example, a liquid, gel, spray or cream form of a disclosed composition or extract is applied substantially evenly across the surface of the skin, forming a layer of the composition or extract on the skin. In some examples, the composition or extract is then gently rubbed into the desired hair follicles or shafts.

Omentum lipid extract compositions and kits for promoting hair growth and/or inhibiting hair loss are also disclosed herein for use in the home or by a clinician. In one example, this kit is suitable for use by a clinician or aesthetician. In such example, the kit can further include applicators to assist with applying the composition. Generally the kit also includes instructions for use. These instructions can be written or in a digital formal (such as a videotape, DVD or CD) for use with electronic devices such as computers, CD players, mp3 players or DVD players and the like. In another example, the kit is suitable for use in the home. This kit can include an applicator, such as a sponge or cloth, for applying the composition. Alternatively, one or more fingers can be used to apply the composition. Generally, the kit also includes instructions for use. These instructions can be written or in a digital format (such as a videotape, DVD or CD) for use with electronic devices such as computers, CD players, mp3 players or DVD players.

In some examples, the kit includes one of the disclosed compositions or extracts and one or more additional hair promoting compounds, such as sodium hyaluronate, either in two separate containers or as a single composition in a single container. In one example, the composition or extract is applied to a target area. In one specific non-limiting example, the omentum lipid extract hair promoting kit can be used by a person in the home as follows. First, a measured quantity of the composition or extract is applied to the surface the skin where hair growth is desired by the use of an applicator, such as a sponge or cloth, or by the use of one or more fingers, to provide an even layer of the composition or extract on the skin surface over the hair follicles where hair growth is desired or desired to be maintained. The composition or extract is either allowed a certain time length to be passively absorbed into the skin surface/hair follicle or absorption of the composition/extract by the skin surface/ hair follicle can be facilitated by gently rubbing the composition into the skin surface/hair follicle with the fingertips. Generally, normal skin and hair care procedures, such as washing and applying additional moisturizing and conditioning agents, can be resumed following application of the omentum lipid composition/extract.

This process can be performed as described twice daily, daily, every other day, bi-weekly, weekly, every other week, or monthly, or for some other interval, such as once every 3 to 5 days. In some examples, the process is performed following washing the skin surface with a solution, such as shampoo.

Desired benefits may include not only hair growth or prevention/inhibition of further hair loss, but the textural qualities of the hair shaft can be improved, including softness, suppleness, and smoothness, leading to enhancement of luster of the hair.

The following examples are provided to illustrate certain particular features and/or embodiments. These examples should not be construed to limit the disclosure to the particular features or embodiments described.

EXAMPLES

Example 1

General Omental Lipid Extract Process

This example describes a general method for omental lipid extraction.

Omentum, such as porcine omentum, is obtained from a United States Department of Agriculture inspected plant where porcine product has passed ante and post mortem inspection. The omentum is free or freed of extraneous material such as muscle so that substantially only omental fat is used in the process. The omentum is rinsed with water, chilled in ice water, and then drained for packaging. The omentum is then frozen into blocks and frozen in a blast freezer, which will freeze solid a 30 to 40 pound block of omentum in 12 hours or less.

To prepare for extraction, the frozen blocks of omentum are removed from the freezer and flaked on hydraflaker to increase surface area of the omental material. After hydraflaking, the frozen omental material will look similar to bark mulch with pieces ranging in length from a powder form to about 0.75 inches.

The flaked material is placed in a container known as a coffin filter for cleaning of the material. A coffin filter may be a container, such as a wooden box, that is approximately 6 ft long and 2 ft. wide with a screen in the bottom of the box to allow for fluid to drain out of the box and a door to allow the screen to be engaged or not. A 2.5% saline solution is added to the omentum in the coffin filter and allowed to soak with the omentum for two to four days. The solution in the coffin box is then drained from the omentum leaving a cleaned omental material.

The omental material is then placed into a heating container and heated to a temperature of between 225 degrees Fahrenheit to 250 degrees Fahrenheit from an original temperature of room temperature (for example, 60 to 80 degrees Fahrenheit). The heating process may take approximately 2 to 4 hours. As the omental material is heated, a liquid oil will form. During this period, solids are continuously removed from the top of the mixture of the liquid oil. Once the omental material has reached a temperature of between 210 degrees Fahrenheit to 250 degrees Fahrenheit, it is maintained at a temperature within that range until the water in the material has been boiled off (which can be visually determined by the lack of steam).

After the water has been evaporated from the oil, the oil is filtered through a filter or filters to remove solid omentum material. The omentum extract filtrate will be a viscous oil. This viscous oil is retained and placed into a container and chilled to a temperature of freezing (about 32 degrees Fahrenheit).

Example 2

Effect of High Temperature on Omentum Extract Process

This example illustrates the effect of temperature on an omentum extract lipid profile.

Porcine omentum was extracted as in Example 1, but the temperature range at which the omental material was observed was greater, from 95 degrees F. to 290 degrees Fahrenheit. At approximately 210 degrees Fahrenheit, the liquid being generated from the omental material by the heating began to become clear. At 215 degrees Fahrenheit there was no visible change. At 225 Fahrenheit, the evaporation of non-lipid material as steam was obvious. At 250 degrees Fahrenheit, the non-lipid liquid had been driven off. At 290 degrees F., the sample turned a beige color indicating burning of the lipid material. This indicates that a method of extraction using a temperature in the range from above 250 degrees Fahrenheit, as the temperature approaches 290 degrees Fahrenheit, will not be useful as the omental lipids burn and degrade in that temperature range.

Example 3

Effect of Temperature on Omentum Extract Process

This example further illustrates the effect of temperature on an omentum extract lipid profile.

Porcine omentum was extracted as in Example 1, with samples of the heated liquid removed from the omental material during heating and tested for the presence of lipids. Samples were removed for testing when the liquid material being heated was at temperatures of 200 degrees Fahrenheit, 210 Fahrenheit, 225 degrees Fahrenheit, 250 degrees Fahrenheit. The samples collected for the four temperatures were placed into containers and sent to a laboratory for lipid analysis. It is also noted that the sample from 225 degrees Fahrenheit was a white substance, while the sample from 250 Fahrenheit had begun to turn to a more yellow color. This indicates that 250 degrees Fahrenheit is the top of the acceptable range for heating the omental material as the yellow color is an indication that the lipid substance is beginning to degrade and will degrade further at temperatures above 250 degrees Fahrenheit.

To perform the lipid analysis, a 50 mg aliquot was removed from each sample container and suspended in 1.5 ml of a mixture of Acetonitrile/Tetrahydrofuran (ACN/THF) 50:50. A small amount of insoluble material was present in the 200 degrees Fahrenheit and 210 degrees Fahrenheit samples, which was removed by centrifugation. The latter two samples (225 degrees Fahrenheit and 250 degrees Fahrenheit) dissolved completely.

The samples were tested for lipid content on a Hewlett-Packard model 1090 HPLC equipped with a Sedex-75 evaporative light scattering detector. The column was a newly purchased Kromasil KR-100 C-8 column 4.6 mm×150 mm. The solvent flow rate was 1.2 ml/min. The solvent was a gradient elution starting at 75/25 ACN/THF, held for 5 minutes then ramped to 100% THF over 15 minutes, then held at 100% THF. The sample volume injected was 10 µl. HPLC tracings for the various samples are illustrated in FIGS. 1-4. The x axis is time (minutes) and the y axis is the number of particles counted by the detector at a given time on the x-axis (normalized as calculated to be expressed in relation to the largest peak present on the chromatogram) and the area under the peaks shows time and intensity of the various components of the omental extract.

The first two samples (200 degrees Fahrenheit/FIG. 1. and 210 degrees Fahrenheit/FIG. 2.) showed the presence of very little lipid. This can be seen in FIGS. 1 and 2. The next two samples (225 degrees Fahrenheit/FIG. 3 and 250 degrees Fahrenheit/FIG. 4), both have a similar profile comprising at least six different lipids as can be seen in the peaks between 7 and 11 in FIGS. 3 and 4.

Example 4

Heat Extraction Superior to Organic Solvent Extraction

This example illustrates the porcine omental extract extracted through the disclosed temperature extraction process results in a greater number of lipids than are present in a composition comprising conventional organic solvent extracted lipids.

Figure 5:
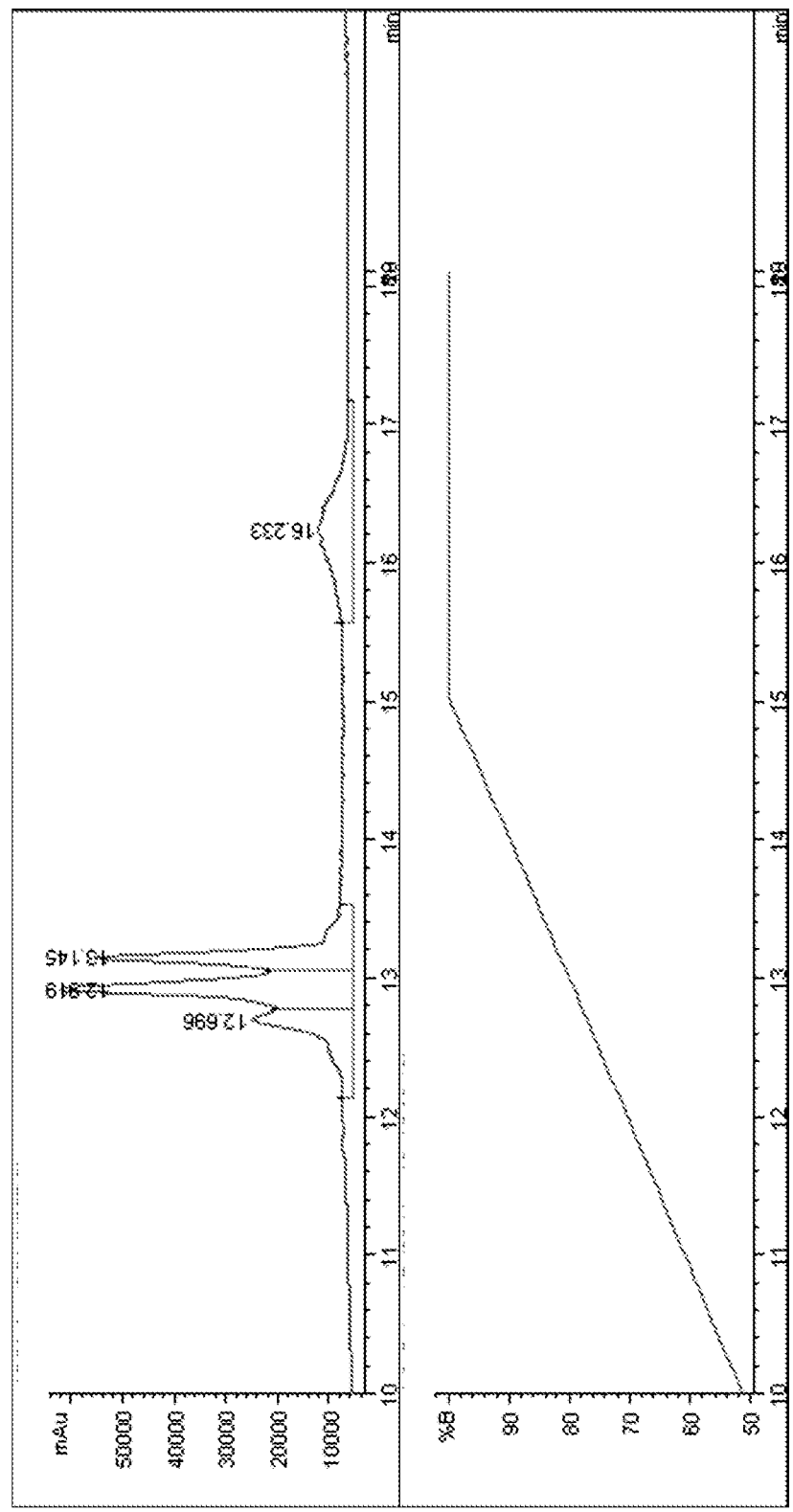
FIG. 5 is a HPLC tracing illustrating an omental lipid extract profile generated from a commercially available skin cream composition (CABOT® POL) containing porcine omental lipids extracted by an organic solvent extraction process. The x axis is time (minutes) and the y axis is milli-absorbance (mAu) and the area under the peaks shows time and intensity of the various components of the omental extract.

FIG. 5 shows a lipid analysis, as conducted in Example 3, for a commercially available skin cream composition (CABOT® POL) containing porcine omental lipids extracted by an organic solvent extraction process using hexane. As can be seen by comparing FIG. 5 to FIGS. 3 and 4 or FIG. 5 to FIGS. 6 and 7, a porcine omental extract extracted through the temperature extraction process disclosed herein contains more numerous lipids than are present in a composition in which the omental lipids were extracted using a conventional organic solvent extracted lipids. A comparison of the HPLC data also indicates, however, that the methods disclosed herein generate an omental extract having a similar lipid profile to a commercial omental product extracted using hexane.

Example 5

Omental Lipid Extract Process

This example describes an additional method for omental lipid extraction.

Porcine Omental Fat (Lace Fat) was collected at a USDA inspected slaughterhouse facility. The intact fat was collected free of extraneous tissue and put in a container of clean ice water. Product was drained, packed, and frozen in 20 or 30 lbs boxes. Product was shipped to the processing facility under frozen conditions. Product was reduced in size by using an approximate ½ "hydroflaker" or ½ grinder plate to increase product surface area. Product was submerged in a bath of 2.5% sodium solution for a period of 24 to 48 hours to extract excess blood from the omentum fat. Product was drained and taken to processing cookers. Product was cooked in a large kettle maintaining a 212 degrees Fahrenheit temperature for 3 hours. Product while being stirred was allowed to reach 220 degrees Fahrenheit until all water vapor was gone. The finished product was agitated as the steam was taken off. Product was pumped through a series of 13⅝ inches diameter discs, which measure 22 micron in pore size. The samples were tested for lipid content on a Hewlett-Packard model 1090 HPLC equipped with a Sedex-75 evaporative light scattering detector. The column was a Kromasil KR-100 C-8 column 4.6 mm×150 mm. The solvent flow rate was 1.2 ml/min. The solvent was a gradient elution starting at 75/25 ACN/THF, held for 5 minutes then ramped to 100% THF over 15 minutes, then held at 100% THF. The sample volume injected was 10 µl.

FIG. 6 illustrates the lipid profile of an omentum extract from a 1 kilogram batch while FIG. 7 illustrates the lipid profile of an omentum extract generated from a 5 kilogram batch. Both samples had similar lipid profiles indicating that the difference in omental volume between the two studies did not significantly alter the lipid yield. These studies indicated the scalability of the process wherein the end product remains the same.

The above-described examples merely disclose particular, specific embodiments of the disclosed compositions and methods. They are not intended to be limiting in any way. Moreover, although these embodiments have been described in detail, those of ordinary skill in the art will understand that variations may be made thereto without departing from the spirit of the invention or scope of the appended claims.

We claim:

1. A method of making a composition comprising an extract of mammalian omentum, comprising:
   preparing omentum for lipid extraction prior to heating the mammalian omentum, wherein preparing the omentum comprises, isolating the omentum from a subject, freezing the isolated omentum, soaking the omentum in a cleaning solution for about 36 hours, wherein the cleaning solution is an about 2.5% saline solution,
   heating the prepared omentum to a temperature of between 210 degrees Fahrenheit and 240 degrees Fahrenheit, and
   extracting the liquid portion of the heated mammalian omentum.

2. The method of claim 1, wherein preparing the omentum comprises soaking the omentum in a 2.5% saline solution for about 36 hours.

3. The method of claim 1, further comprising purifying the extracted liquid portion.

4. The method of claim 3, wherein purifying the extracted liquid portion comprises filtering the extracted liquid portion through a filter press comprising a series of two or more 13⅝ inches diameter, 22 micron pore-sized filters to remove solid omentum material.

5. The method of claim 1, wherein heating the prepared omentum comprises heating the prepared omentum to a temperature of between 212 degrees Fahrenheit and 225 degrees Fahrenheit.

6. The method of claim 1, wherein heating the prepared omentum comprises heating the prepared omentum to a temperature of between 215 degrees Fahrenheit and 220 degrees Fahrenheit.

7. The method of claim 1, wherein heating the prepared omentum comprises heating the prepared omentum in the absence of an organic solvent.

8. The method of claim 1, wherein the omentum is porcine omentum.

\* \* \* \* \*